United States Patent
Chupakhin et al.

(10) Patent No.: US 6,313,111 B1
(45) Date of Patent: Nov. 6, 2001

(54) SUBSTITUTED 6H-1,3,4-THIADIAZINE-2-AMINES, THE USE THEREOF AS ANAESTHETISING, CARDIOVASCULAR AND HYPOMETABOLIC AGENTS, AND PHARMACEUTICAL COMPOSITION CONTAINING THEM

(75) Inventors: Oleg Nikolaevich Chupakhin; Larisa Petrovna Sidorova; Emma Afanasievna Tarakhty; Antonina Petrovna Novikova; Natalya Mikhailovna Perova, all of Ekaterinburg; Valentin Antonovich Vinogradov, Moscow, all of (RU); Michiel Franciscus van Ginkel, Amstelveen (NL)

(73) Assignees: The Procter & Gamble Company, Cincinnati, OH (US); Nauchno-Tekhnologicheskoe Predpriyatie "Ligand" (Tovarischestvo S Ogranichennoi Otvetstvennostiju), Ekaterinburg (RU)

( * ) Notice: Subject to any disclaimer, the term of this patent is extended or adjusted under 35 U.S.C. 154(b) by 0 days.

(21) Appl. No.: 09/101,078
(22) PCT Filed: Dec. 28, 1995
(86) PCT No.: PCT/RU95/00284
  § 371 Date: Dec. 8, 1998
  § 102(e) Date: Dec. 8, 1998
(87) PCT Pub. No.: WO97/24352
  PCT Pub. Date: Jul. 10, 1997
(51) Int. Cl.$^7$ .................. A61K 31/382; A61K 31/54
(52) U.S. Cl. ................ 514/222.5; 514/217.05; 514/236.2; 544/8
(58) Field of Search .............. 514/222.5, 217.05, 514/236.2; 544/8

(56) References Cited

U.S. PATENT DOCUMENTS

| | | | |
|---|---|---|---|
| 4,272,532 | 6/1981 | Jones et al. | 424/246 |
| 4,309,426 | 1/1982 | Jones, Jr. et al. | 424/246 |
| 4,940,790 | 7/1990 | Thorwart et al. | 544/8 |
| 5,021,413 | 6/1991 | Terada et al. | 514/227.5 |
| 5,411,955 | 5/1995 | Strasser et al. | 514/214 |

FOREIGN PATENT DOCUMENTS

| | | |
|---|---|---|
| 884990 | 12/1980 | (BE) . |
| 884991 | 12/1980 | (BE) . |
| 220311 | 3/1985 | (DD) . |
| 228248 | 10/1985 | (DD) . |
| 3031703 | 3/1981 | (DE) . |
| 3042295 | 6/1982 | (DE) . |
| 2493844 | 5/1982 | (FR) . |
| 2215206 | 9/1989 | (GB) . |
| 49/88889 | 8/1974 | (JP) . |
| 6/253976 | 9/1994 | (JP) . |
| 94/007001 | 12/1995 | (RU) . |
| 94007001 | 12/1995 | (RU) . |
| 1189862 | 11/1985 | (SU) . |
| 1827257 | 11/1985 | (SU) . |
| 1726478 | 4/1992 | (SU) . |

OTHER PUBLICATIONS

Usoltseva S.V., et al. "1,3,4–Thiadiazines: Method of Synthesis and Reactivity." Khim. Geterotsikl. Soedin No. 4 (1991) pp. 435–448 and English comments thereon.

Novikova A.P., et al. "Synthesis and Properties of Functional Derivatives of 1,3,4. Thiadizines . . . " Khim. Geterotsikl. Soedin No: 11 (1991) pp. 1443–1457 and English comments thereon.

Rasina L.N., et al., "On Some Mechanisms of Action of Radioprotectors of Various Chemical Classes in Intestinal Syndrome" Radiobiologiya, 30(2) (1990) pp. 162–165 and English comments thereon.

Belik A.V. et al., "Prediction of A Class of Strong Toxicity of 1,3,4–Thiadiazine Derivatives" Khim–Farm. Zh., 26(3), (1992) pp. 62–64 and English comments thereon.

Perova N.M. et al., "Transformation of 2–Cycloalkylimino–6H–1–3–4Thiadiazines under UV Irradiation" Khim. Geterotsikl. Soedin., No. 4, (1993) pp. 565–600 And English comments thereon.

Patent Abstracts of Japan of JP 06253976 Dated Sep. 13, 1994.

(List continued on next page.)

*Primary Examiner*—John M. Ford
(74) *Attorney, Agent, or Firm*—Ladas & Parry

(57) ABSTRACT

Substitued 6H-1,3,4-thiadiazin-2-amines of the following general formula:

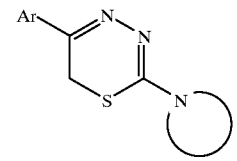

wherein Ar is phenyl optionally substituted with one or more chloro, bromo atoms, $C_1$–$C_4$ alkoxy, or $C_1$–$C_4$ alkyl groups; and

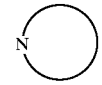

represents a morpholino, thimomorpholino, piperidino, pyrrolidino, or hexamethylenimino moieties, the pharmaceutically acceptable salts thereof and the use of them anasethetic, cardiovascular and hypometabolic agents and pharmaceutical compositions containing them.

4 Claims, No Drawings

OTHER PUBLICATIONS

The Union of Soviet Socialist Republics, The State Patent Office of the USSR (Gospatent of the USS) Abstract of the Specification of SU 1827257 dated Jul. 15, 1993.

Russian Patent Office Re: No. 2403/128935 Abstract of the Description of the Invention to Inventor's Certificate of SU 1189862 dated Nov. 7, 1985.

Textbook of Anesthesiology, The Meditsina Publishers, Moscow (1994) pp 10–13 (English & Russian Translation.).

Osipova, N.A. "Evaluation of the Effect of Narcotic, Analgetic and Psychotropic Agents in Clinical Anesthesiology." The Meditsina Publishers, Leningrad, Chapter 2 (1988) pp 14–16 (English & Russian Translation).

"Side Effects of Drugs." The Meditsina Publishers, Moscow (1983) pp 1–6 (English & Russian Translation).

SUBSTITUTED 6H-1,3,4-THIADIAZINE-2-AMINES, THE USE THEREOF AS ANAESTHETISING, CARDIOVASCULAR AND HYPOMETABOLIC AGENTS, AND PHARMACEUTICAL COMPOSITION CONTAINING THEM

This application is a 371 of PCT/RU95/00284.

TECHNICAL FIELD

The present invention relates to novel 6H-1,3,4-thiadiazine-2-amines, to their use in medicine or veterinary as anaesthetic, cardiovascular and hypometablic agents and to pharmaceutical compositions containing them.

BACKGROUND OF THE INVENTION

Anaesthesia can generally be described as a state in which noxious events such as surgical procedures are rendered imperceptible by the body, the state being accompanied either by loss of consciousness (general anaesthesia) or no loss of consciousness (local anaesthesia). A complete or general anaesthetic given by inhalation or intravenous route produces a state of profound sleep and loss of motor activity (hypnosis), analgesia, muscle relaxation and protection against the increase in blood pressure and heart rate resulting from surgical stress. Anaesthetics generally display hypometabolic activity and frequently act as respiratory or cardiovascular depressants. Certain anesthetics can be used to produce deliberate hypotensive effects which are very valuable in intracranial and other surgical procedures. Although a large number of agents having anaesthetic and cardiovascular activity have been identified and/or commercialised, there is a continuing need for new materials having hypomethabolic activity, which are valuable for inducing sleep, reduction in motor activity, hypotension, bradycardiac, hypocoagulative, anti-aggregant and other hypobiosis effects such as reduced oxygen consumption and reduced body temperature, which would be valuable for used in complex surgical procedures or in the treatment of life threatening and/or traumatic situations such as brain stroke and myocardial infarction, and which have excellent potency, duration and CNS and cardiovascular toxicity profiles with absence of side effects such as tremor, consulvions and irregular breathing and heart beat.

There is considerable body of data concering 6-R-1,3,4-thiadiazin-2-amines (for reviews see [1–3]). Also a patent literature provides data on myo-relaxant [4–7], sedative [8,9], spasmolytic [10–12] and other types of biological activity [3]. A number of 5-aryl derivatives of 1,3,4-thiadiazines have been specifically described in the art [14–20] as well as 6-alkyl and 6-phenyl analogs thereof [13 and 21]. The value of 6H-1,3,4-thiadiazin-2-amines as hypometabolic anaesthetic and cardiovascular agents has not hitherto been recognised however. Moreever, many of these compounds are apparently novel and have not been previously described in the literature.

The prior art on 6-R-1,3,4-thiadiazin-2-amines includes:

1. H. Beyer, Z. Chem., Bd. 9, S. 361, (1969).
2. S.V. Usoltseva, G.P. Andronnikova, and V.S. Mokreushin, Khim. Geterotsikl. Soedin., No 4, 435, (1991).
3. A.P. Novikova, N. M. Perova, and O. N. Chupakhin, Khim. Geterotsikl. Soedin., No 11, 1443, (1991)
4. W. D. Jones and F. P. Miller. US-A-4,309,426 (1982).
5. W. D. Jones and F. P. Miller. BE-A-884,991 (1980).
6. W. D. Jones and F. P. Miller. DE-A-3,042,295 (1982).
7. FR-A-2,493,844 (1982).
8. US-A-4,272,532 (1981).
9. F. P. Miller and W. D. Jones. BE-A-884,990 (1980).
10. W. D. Jones and F. P. Miller. DE-A-3,031,703 (1981).
11. Fisons PLC, Japan Kokai, Tokyo Koho JP-A-6253976.
12. W. P. Pfeiffer and E. Bulka, DD-A-220311 (1985).
13. N. Yoshida, K. Tanaka, and Y. Iizuka. Japan Kokai 7488889 (1974).
14. L. N. Rasina, O. N. Chupakhin and M. V. Chibiryak. Radiobiologiya, 30(2), 162-5 (1990).
15. A. V. Belik et al, Khim.-Farm. Zh., 26(3), 62–64 (1992).
16. N. M. Perova et al, Khim. Geterotsikl. Soedin., No 4, 565-6 (1993).
17. E Bulka and W. D. Pfeiffer. DD-A-288824.
18. W. D. Pfeiffer and E Bulka, Synthesis, No 7, 485–486 (1977).
19. T. Werner et al, US-A-4,940,790 (1990).
20. A. P. Novikova et al, SU-A-1726478.
21. E. Bulka et al, DD-A-228248.

SUMMARY OF THE INVENTION

According to one aspect of the invention, there is provided the use of substitued 6H-1,3,4-thiadiazin-2-amines of the following general formula as anaesthetic, cardiovascular and hypometabolic agents:

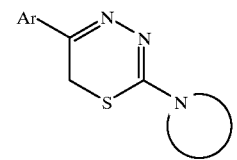

wherein Ar is phenyl optionally substituted with one or more chloro, bromo atoms, $C_1$–$C_4$ alkoxy or $C_1$–$C_4$ alkyl groups; and wherein

represents a morpholino, thiomorpholino, piperidino, pyrrolidino, or hexamethylenimino moiety.

According to the further aspect of the invention, there are provided pharmaceutical composition which includes one ore more of substituted 6H-1,3,4-thiadiazin-2-amines as defined above or pharmaceutically acceptable salts thereof.

According to the still further aspect of the invention, there are provided certain novel substituted 6H-1,3,4-thiadiazin-2-amines of the general formula set out above. Novel compounds of this class include compounds in which

represents thiomorpholino moiety; compounds in which Ar is phenyl substituted with one or more bromo atoms, $C_1$–$C_4$ alkoxy or $C_1$–$C_4$ alkyl groups, and

represents piperidino, pyrrolidino moiety; and compounds in which Ar is phenyl substituted at the 2 or 3 positions with one or more bromo atoms, $C_1$–$C_4$ alkoxy or $C_1$–$C_4$ alkyl groups, and

represents morpholino.

DISCLOSURE OF THE INVENTION 1,3,4-Thiadiazines suitable for the use according to the present invention contain at the 5 position of the thiadiazine ring unsubstituted phenyl or phenyl substituted with one or more straight or branched chain $C_1$–$C_4$ alkyl, alkenyl, alkoxy or acyloxy groups, or one or more hydroxy groups or halogen atoms. In preferred compounds, Ar represents unsubstituted phenyl or phenyl substituted with one or more alkyl, alkoxy groups, or chloro or bromo atoms. Moreover said compounds are substituted at the 2 position of the thiadiazine ring with a cycloalkylimine moiety, preferably selected from morpholino, thiomorpholino, piperidino, pyrrolidino and hexamethylenimino.

The invention further relates to a process for the preparation of the 1,3,4-thiadiazines described herein in with an α-haloarylalkanone having the formula Ar—CO—CH($R^1$)X is reacted with a thiosemicarbazide of formula

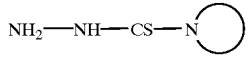

wherein X is halo, preferably chloro or bromo, and Ar, $R^1$ and

are as defined above.

According to the present invention the 1,3,4-thiadiazines may be isolated and/or used in free from or converted into additive salts with pharmacologically acceptable mineral or organic acids. Suitable for the preparation of acid addition salts are, for example, mineral acids, such as hydrobromic acid, hydrochloric acid, sulfuric acid or phosphoric acid; organic carboxylic acids, such as acetic acid, lactic acid, maleic acid, fumaric acid, oxalic acid, tartaric acid, citric acid or gluoconic acid; or organic sulfonic acids, such as benzenesulfonic acid, p-toluenesulfonic acid, methanesulfonic acid, trifluoromethanesulfonic acid and cyclohexylamidosulfonic acid.

The α-haloarylalkanone used as starting materials in the manufacture of the thiadiazines described above are known from the literature or may be prepared starting from arylalkanones by the reaction with a suitable halogenating agent according to the methods described in Houben-Weyl, Vol. E4 (1960), pp. 171–189. Suitable compounds are, for example, α-bromarylethanones in which aryl may be selected from phenyl and substituted phenyl and prepared by halogenating the correspondent substituted 1-arylalkanoes with bromine or copper (II) bromide according to the method of King and Ostrum, J. Org. Chem. 29 (1964), pp. 3459–3461.

The substituted thiosemicarbazides which are used as starting materials are generally known in the art or they may be prepared by the methods described in Houben-Weyl, Vol. E4, pp. 506–515, and by K. Jensen et al., Acta Chem. Scand. 22 (1968), pp. 1–50. Thus, the thiosemicarbazides may be obtained by adding hydrazine to isothiocyanates or by the reaction of suitable N,N-di-substituted thiocarbamoyl chlorides with hydrazine or by the reaction of ethyl dithiocarbarates of formula

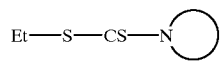

with hydrazine. In order to avoid interfering side reactions, said preparations are advantageously carried out in aprotic solvents, such as, for example, chloroform, tetrachloromethane, diethyl ether or dioxan.

The reaction of α-haloarylalkanones with thiosemicarbazide is expediently carried out using equimolar amounts of the two reactants in a solvent or in a diluent which are inert towards the reagents. Suitable for this purpose are, in particular, lower alcohols, such as methanol, ethanol, n-propanol, isopropanol and the various butanols, or ethylacetate, and mixtures thereof, however ethanol is preferable. The reaction is generally carried out at temperatures in the range from about 20° C. to the temperature of the reflux of the reaction mixture, preferably at about 20° C. to 70° C. Depending on the reactivity of the reagents, the type of the reaction medium and the reaction temperature, reaction time may be in the range from about 5 minutes to 2 hours. The final products usually recrystallize in analytically pure form on slow cooling of the reaction mixture.

Depending on their solubility the compounds may be administered either by oral route or via parenteral injection in the forms of their solutions. They may be administered either alone, for example in the form of microcapsules, as well as in mixtures with one another or in combination with suitable adjuvants and/or excipients.

The present invention further relates to pharmaceutical compositions which comprise at least one of thiadiazine compounds as defined above, or one of acid addition salts thereof, and which contain at least one of said active compounds with pharmaceutically suitable and physiologically acceptable excipients, diluents and/or other adjuvants. Suitable solid or liquid galenic formulations include, for example, granules, powders, coated tablets, tablets, (micro) capsules, suppositories, syrups, elixirs, suspensions, emulsions, drops of injectable solutions, and also preparations having a protracted release of active compound, in the disintegrants, binders, coating agents, swelling agents, glidants, lubricants, flavors, sweeteners or solubilizers are usually used. Suitable adjuvants include, for example, magnesium carbonate, titanium dioxide, lactose, mannitol and other sugars, talc, lactalbumin, gelatine, starch, cellulose and derivatives thereof, animal and vegetable oils, polyethylene glycols and solvents such as sterile water and monohydric or polyhydric alcohols, for example glycerol.

The pharmaceutical preparations are preferably manufactured and administered for treating in dosage units, each of them contains as active component a certain dose of at least one of thiadiazine compounds and/or at least one of corresponding acid addition salts thereof. In the case of injectable solutions, the thiadiazine is preferably administered in dosages in the range from about 10 to about 600, preferably from about 20 to about 500, more preferably from about 30 to about 400 mg/kg.

Compounds suitable for use herein are represented by the following examples:

1. 2-Morpholino-5-phenyl-6H-1,3,4-thiadiazine, hydrobromide,
2. 2-Morpholino-5-phenyl-6H-1,3,4-thiadiazine, mesilate,
3. 2-Morpholino-5-(4-chlorophenyl)-6H-1,3,4-thiadiazine, hydrobromide,
4. 2-Morpholino-5-(3-bromophenyl)-6H-1,3,4-thiadiazine, hydrobromide,
5. 2-Thiomorpholino-5-phenyl-6H-1,3,4-thiadiazine, hydrobromide,
6. 2-Thiomorpholino-5-phenyl-6H-1,3,4-thiadiazine, mesilate,
7. 2-Thiomorpholino-5-(4-ethoxypenyl)-6H-1,3,4-thiadiazide, hydrobromide,
8. 2-Thiomorpholino-5-(3-bromophenyl)-6H-1,3,4-thiadiazine, hydrobromide,
9. 2-Thiomorpholino-5-(4-methoxypehnyl)-6H-1,3,4-thiadiazine, hydrobromide,
10. 2-Thiomorpholino-5-(2-chlorophenyl)-6H-1,3,4-thiadiazine, hydrobromide,
11. 2-Thiomorpholino-5-(4-chlorophenyl)-6H-1,3,4-thiadiazine, hydrobromide,
12. 2-Hexamethylenimino-5-phenyl-6H-1,3,4-thiadiazine, hydrobromide,
13. 2-Piperidino-5-phenyl-6H-1,3,4-thiadiazine, hydrobromide,
14. 2-Pyrrolidino-5-phenyl-6H-1,3,4-thiadiazine, hydrobromide,
15. 2-Hexamethylenimino-5-(4-bromophenyl)-6H-1,3,4-thiadiazine, hydrobromide,
16. 2-Hexamethylenimino-5-(4-chlorophenyl)-6H-1,3,4-thiadiazine, hydrobromide,
17. 2-Hexamethylenimino-5-(4-bromophenyl)-6H-1,3,4-thiadiazine, mesilate,
18. 2-Morpholino-5-(2-chlorophenyl)-6H-1,3,4-thiadiazine, hydrobromide.

EXAMPLES

All compounds herein were obtained in 60–80% yields by condensation of α-naloketones with the corresponding 4-substituted thiosemicarbazides, proceeding smoothly on heating in ethanol. Evidence for the structure of the compounds is provided by their spectral data (UV, IR, $^1$H NMR); their purity is confirmed by thin-layer chromatography and elemental analysis.

Example 1

2-Morpholino-5-phenyl-6H-1,3,4-thiadiazine, hydrobromide.

The compound 1 was prepared by heating of 2 g (0.01 mole) of α-bromacetophenone with 1.6 g (0.01 mole) of morpholide of thiocarbazinic acid in 20 ml of absolute ethanol for 30 minutes. The product obtained after cooling was filtered off and recrystallized twice with active charcoal. Yield 1.8 g (75%). M.p. 191–192° C. $R_f$=0.35 (eluent: butanol-acetic acid-water 4:1:5). Found, %: C 45.7; H 4.7; N 12.1. $C_{13}H_{16}BrN_3OS$. Calcualted %: C 45.6; H 4.7; N 12.3. $^1$H NMR, DMSO-$d_6$, δ, ppm: 3.85 (8H, m, morpholino); 4.45 (2H, s, $CH_2S$); 7.45–8.1 (5H, m, $C_6H_5$).

Example 2

2-Morpholino-5-phenyl-6H-1,3,4-thiadiazine, mesilate

Methanesulfonic acid, 0.4 g (0.004 mole), was added dropwise to a solution of 1 g (0.004 mole) of the compound 1 in 70 ml of dry ether. A colourless precipitate formed after 20 minutes of stirring was filtered off and recrystallized from absolute ethanol. Yield 1.2 g (88%). M.p. 173–174° C. $R_f$=0.38 (eluent: butanol-acetic acid-water 4:1:5). Found, %: C 47.0; H 5.5; N 11.6 $C_{14}H_{19}N_3O_4S_2$. Calculated, %: C 47.1; H 5.3; N 11.8. $^1$H NMR, DMSO-$d_6$, δ, ppm: 2.30 (3H, s, $SCH_3$); 3.82 (8H, m, morpholino); 4.29 (2H, s, $CH_2S$); 7.4–8.0 (5H, m, $C_6H_5$).

Example 3

2-Morpholino-5-(4-chlorophenyl)-6H-1,3,4-thiadiazine, hydrobromide.

The compound 3 was prepared in the same manner as in Example 1. Yield 67%. M.p. 242–243° C. $R_f$=0.37 (eluent: butanol-acetic acid-water 4:1:5). Found, %: C 41.7; H 4:1; N 11.4. $C_{13}H_{15}BrClN_3OS$. Calculated, %: C 41.7; H 4.0; N 11.2. $^1$H NMR, DMSO-$d_6$, δ, ppm: 3.85 (8H, m, morpholino): 4.40 (2H, s, $CH_2S$); 7.70 and 7.90 (4H, dd, $C_6H_4$).

Example 4

2-Morpholino-5-(3-bromophenyl)-6H-1,3,4-thiadiazine, hydrobromide.

The compound 4 was prepared in the same manner as in Example 1 starting from 3-bromo-α-bromoacetophenone and morpholide of thiocarbazinic acid. Yield 70%. M.p. 191–192° C. $R_f$=0.3 (elunet: butanol-acetic acid-water 4:1:5). Found, %: C 37.4; H 3.6 $C_{13}H_{15}Br_2N_3OS$. Calculated, %: C 37.1; H 3.6. $^1$H NMR, DMSO-$d_6$, δ, ppm: 3.80 (8H, m, morpholino); 4.29 (2H, s, $CH_2S$); 7.3–8.2 (4H, m, $C_6H_4$).

Example 5

2-Thiomorpholino-5-phenyl-6H-1,3,4-thiadiazine, hydrobromide.

The compound 5 was prepared by heating of 2 g (0.01 mole) of α-bromacetophenone with 1.8 g (0.01 mole) of thiomorpholinide of thiocarbazinic acid in 25 ml of absolute ethanol in the presence of 1.2 ml of concentrated HBr for 20 minutes. The mixture was cooled with ice to give a yellow precipitate which was filtered off, recrystallized from absolute ethanol and dried. Yield 2.8 g (78%). M.p. 183–184° C. $R_f$=0.51 (eluent: butanol-acetic acid-water 4:1:5). Found %: C 43.7; H 4.6; N 11.7. $C_{13}H_{16}BrN_3S_2$. Calculated, %: C 43.6; H 4.5; N 11.7. $^1$H NMR, DMSO-$d_6$, δ, ppm: 2.9 (4H, m, $N(CH_2)_2$, thiomorpholino); 4.15 (4H, m, $S(CH_2)_2$, thiomorpholino); 4.42 (2H, s, $CH_2S$); 7.4–8.1 (5H, m $C_6H_5$).

Example 6

2-Thiomorpholino-5-phenyl-6H-1,3,4-thiadiazine, mesilate.

Methanesulfonic acid, 0.4 g (0.004 mole), was added dropwise to a solution of 1 g (0.004 mole) of the compound 5. A colourless crystalline product obtained after 15 minutes of stirring was filtered off and recystallized from a mixture of absolute ethanol and dry ether 1:4. Yield 1.2 g (89%). M.p. 160–160° C. $R_f$=0.43 (eluent: butanol-acetic acid-water 4:1:5). Found, %: C 44.9; H 5.0; N 11.4. $C_{14}H_{19}N_3O_3S_3$. Calculated, %: C 45.0; H 5.1; N 11.3. $^1$H NMR, DMSO-$d_6$, δ, ppm: 2.30 (3H, s, $SCH_3$); 2.88 [4H, m, $N(CH_3)_2$, thiomorpholino]; 4.15 [4H, m, $S(CH_2)_2$, thiomorpholino]; 4.31 (2H, s, $SCH_2$); 7.4–8.1 (5H, m, $C_6H_5$).

Example 7

2-Thiomorpholino-5-(4-ethoxyphenyl)-6H-1,3,4-thiadiazine, hydrobromide.

The compound 7 was prepared by heating of 0.7 g (0.003 mole) of α-bromo-4-ethoxyacetophenone with 0.5 g (0.003 mole) of thiomorpholide of thiocarbazinic acid in 15 ml of absolute ethanol in the presence of 0.3 ml of concentrated HBr for 20 minutes. The mixture was cooled with ice to give a yellow precipitate which was filtered off, recystallized from absolute ethanol and dried. Yield 0.8 g (70%). M.p. 169–170° C. $R_f$=0.33 (eluent: butanol-acetic acid-water 4:1:5). Found, %: C 45.0; H 5.2; N 10.3. $C_{15}H_{20}BrN_3OS_2$. Calculated, %: C. 44.8; H 5.0; N 10.4. $^1$H NMR, DMSO-$d_6$, δ, ppm: 1.32 (3H, t, $CH_3$); 2.88 [4H, m, $N(CH_2)_2$, thiomorpholino]; 4.12 [4H, m, $S(CH_2)_2$, thiomorpholino]; 4.26 (2H, q, $OCH_2$—); 4.37 (2H, s, $CH_2S$); 7,5 (4H, dd, $C_6H_4$).

Example 8

2-Thiomorpholino-5-(3-bromophenyl)-6H-1,3,4-thiadiazine, hydrobromide.

The compound 8 was prepared by heating of 0.8 g (0.003 mole) of α-bromo-3-bromoacetophenone with 0.5 g (0.003 mole) of thiomorpholinide of thiocarbazinic acid in 20 ml of absolute ethanol in the presence of 0.3 ml of concentrated HBr for 15 minutes. The mixture was cooled with ice to give a yellow precipitate which was filtered off, recystallized from absolute ethanol and dried. Yield 0.75 g (64%). M.p. 198–199° C. $R_f$=0.23 (eluent: butanol-acetic acid-water 4:1:5). Found, %: C 36.3; H 3.6. Si 9.8. $C_{13}H_{15}Br_2N_3S_2$. Calculated, %: C 35.7; H 3.4; N 9.6. $^1$H NMR, DMSO-$d_6$, δ, ppm: 2.88 [4H, m, $N(CH_2)_2$, thiomorpholino]; 4.15 [4H, m, $S(CH_2)_2$, thiomorpholino]; 4.33 (2H, s, $CH_2S$); 7.35–8, 14 (4H, m, $C_6H_{14}$).

Example 9

2-Thiomorpholino-5-(4-methoxyphenyl)-6H-1,3,4-thiadiazine, hydrobromide

The compound 9 was prepared in the same manner as in Example 5 starting from 4-methoxyphenyl-α-bromoacetophenone and thiomorpholide of thiocarbazinic acid. Yield 77%. M.p. 201–202° C. $R_f$=0.35 (eluent: butanol-acetic acid-water 4:1:5). Found, %: C 43.6; H 4.7; N 10.9. $C_{14}H_{18}BrN_3OS_2$. Calculated, %: C 43.3; H 4.6: N 10.8. $^1$H NMR, DMSO-$d_6$, δ, ppm: 2.88 [4H, m, $N(CH_2)_2$, thiomorpholino]; 3.85 (3H, s, $OCH_3$); 4.12 [4H, m, $S(CH_2)_2$, thiomorpholino]; 4.32 (2H, s, $Ch_2S$); 7.5 (4H, dd, $C_6H_4$).

Example 10

2-Thiomorpholino-5-(2-chlorophenyl)-6H-1,3,4-thiadiazine, hydrobromide

The compound 10 was prepared by heating of 0.7 g (0.003 mole) of α-bromo-2-chloroacetophenone with 0.5 g (0.003 mole) of thiocarbazinic acid thiomorpholide in 30 ml of absolute ethanol in the presence of 0.3 ml of concentrated HBr for 30 minutes. After cooling with ice 30 ml dry ether was added to the reaction mixture, yielding a yellow precipitate which was filtered off, recystallized from absolute ethanol and dried. Yield 0.85 g (71%). M.p. 190–191° C. $R_f$=0.38 (eluent: butanol-acetic acid-water 4:1:5). Found, %: C 39.8; H 4.2; N 10.6. $C_{13}H_{15}BrClN_3S_2$. Calculated, %: C 39.7; H 3.8; N 10.7. $^1$H NMR, DMSO-$d_6$, δ, ppm: 2.88 [4H, m, $N(CH_2)_2$, thiomorpholino]; 4.15 [4H, m, $S(CH_2)_2$, thiomorpholino]; 4.25 (2H, s, $CH_2S$); 7.4–7.8 (4H, dd $C_6H_4$).

Example 11

2-Thiomorpholino-5-(4-chlorophenyl)-6H-1,3,4-thiadiazine, hydrobromide

The compound 11 was prepared by heating of 2.3 g (0.01 mole) of α-bromo-4-chloroacetophenone with 1.8 g (0.01 mole) of thiomorpholide of thiocarbazinic acid in 50 ml of absolute ethanol for 25 minutes. The mixture was cooled with ice to give a yellow precipitate which was filtered off, recrystallized from absolute ethanol and dried. Yield 3.0 g (77%). M.p. 201–202° C. $R_f$=0.50 (eluent: butanol-acetic acid-water 4:1:5). Found, %: C 40.0; H 4.2; N 10.06. $C_{13}H_{15}BrClN_3S_2$. Calculated, %: C 39.7; H 3.8; N 10.7. $^1$H NMR, DMSO-$d_6$, δ, ppm: 2.88 [4H, m, $N(CH_2)_2$, thiomorpholino]; 4.18 [4H, m, $S(CH_2)_2$, thiomorpholino]; 4.39 (2H, s, $CH_2S$); 7.3 (4H, dd, $C_6H_4$).

Example 12

2-Hexamethylenimino-5-phenyl-6H-1,3,4-thiadiazine, hydrobromide

The compound 12 was prepared in the same manner as in Example 5 starting from α-bromoacetophenone and 4,4-hexamethyleniminothiosemicarbazide. Yield 68%. M.p. 203–204° C. $R_f$=0.42 (eluent: butanol-acetic acid-water 4:1:5). Found, %: C 50.6; H 5.6; N 11.6. $C_{15}H_{20}BrN_3S$. Calculated, %: C 50.8; H 5.6; N 11.9. $^1$H NMR, DMSO-$d_6$, δ, ppm: 1.4–2.2 [8H, m, $(CH_2)_4$, hexamethylenimino]; 3.7–4.2 [4H, m, $N(CH_2)_2$, hexamethylenimino]; 4.48 (2H, s, $CH_2S$); 7.5–8.1 (5H, m, $C_6H_5$).

Example 13

2-Piperidino-5-phenyl-6H-1,3,4-thiadiazine, hydrobromide

The compound 13 was prepared in the same manner as in Example 5 starting from α-bromoacetophenone and 4,4-pentamethyleniminothiosemicarbazide. Yield 68%. M.p. 230–232° C. $R_f$=0.7 (eluent: butanol-acetic acid-water 4:1:5). Found, %: C 49.5, H 5.4; N 12.4. $C_{14}H_{18}BrN_3S$. Calculated, %: C 49.4, H 5.3, N 12.4. $^1$H NMR, DMSO-$d_6$, δ, ppm: 1.5–2.2 [6H, m, $(CH_2)_4$, piperidino]; 3.5–3.8 [4H, m, $N(CH_2)_2$, piperidino]; 4.35 (2H, s, $CH_2S$); 7.2–8.1 (5H, m, $C_6H_5$).

Example 14

2-Pyrrolidino-5-phenyl-6H-1,3,4-thiadiazine, hydrobromide

The compound 14 was prepared in the same manner as in Example 5 starting from α-bromoacetophenone and 4,4-tetramethyleniminothiosemicarbazide. Yield 78%. M.p. 182–183° C. $R_f$=0.49 (eluent: butanol-acetic acid-water 4:1:5). Found, %: C 47.6; H 4.9; N 12.9. $C_{13}H_{18}BrN_3S$. Calculated, %: C 47.9; H 5.0; N 12.9. $^1$H NMR, DMSO-$d_6$, δ, ppm: 2.1 [4H, m, $(CH_2)_2$, pyrrolidino]; 3.7 [4H, m, $N(CH_2)_2$, pyrrolidino]; 4.45 (2H, s, $CH_2S$); 7.4–8.0 (5H, m, $C_6H_5$).

Example 15

2-Hexamethylenimino-5-(4-bromophenyl)-6H-1,3,4-thiadiazine, hydrobromide

The compound 15 was prepared in the same manner as in Example 5 starting from α-bromo-4-bromoacetophenone and 4,4-hexamethyleniminothiosemicarbazide. Yield 75%. M.p. 201-14 203° C. $R_f$=0.38 (eluent: butanol-acetic acid-water 4:1:5). Found, %: C 42.0; H 4.6; N 9.4. $C_{15}H_{19}Br_2N_3S$. Calculated, %: C 41.6; H 4.4; N 9.7. $^1$H NMR, DMSO-$d_6$, δ, ppm: 1.4–2.3 [3H, m, $(CH_2)_4$, hexamethylenimino]; 3.6–4.1 [4H, m, $N(CH_2)_2$, hexamethylenimino]; 4.5 (2H, s, $CH_2S$); 7.8 (4H, dd, $C_6H_4$).

Example 16

2-Hexamethylenimino-5-(4-chlorophenyl)-6H-1,3,4-thiadiazine, hydrobromide

The compound 16 was prepared in the same manner as in Example 5 starting from α-bromo-4-chloroacetophenone and 4,4-hexamethyleniminothiosemicarbazide. Yield 68%. M.p. 199–200° C. $R_f$=0.30 (eluent: butanol-acetic acid-water 4:1:5). Found, %: C 46.4; H 5.2; N 10.6. $C_{15}H_{19}BrClN_3S$. Calculated, %: C 46.3; H 4.9; N 10.8. $^1$H NMR, DMSO-$d_6$, δ, ppm: 1.4–2.3 (8H, m, $(CH_2)_4$, hexamethylenimino); 3.6–4.2 [4H, m, $N(CH_2)_2$, hexamethylenimino]; 4.47 (2H, s, $CH_2S$); 7.75 (4H, dd, $C_6H_4$).

Example 17

2-Hexamethylenimino-5-(4-bromophenyl)-6H-1,3,4-thiadiazine, mesilate

Methanesulfonic acid, 0.4 g (0.004 mole), was added dropwise to the solution of 1.5 g (0.004 mole) of the compound 15, and the reaction mixture was stirred at room temperature for 30 minutes. A colourless crystalline product obtained was filtered off and recrystallized from absolute ethanol. Yield 1.7 g (89%). M.p. 201–202° C. $R_f$=0.26 (eluent: butanol-acetic acid-water 4:1:5). Found, %. C. 42.7; H 4.9; N 14.1. $C_{16}H_{22}BrN_3O_3S_2$. Calculated, %: C. 42.9; H 4.9; N 14.3 $^1$H NMR, DMSO-$d_6$, δ, ppm: 1.38–2.05 [8H, m, $(CH_2)_4$, hexamethylenimino]; 2.35 (3H, s, $SCH_3$); 3.6–4.0 [4H, m, $N(CH_2)_2$, hexamethylenimino]; 4.35 (2H, s, $CH_2S$); 7.80 (4H, dd, $C_6H_4$).

Example 18

2-Morpholino-5-(2-chlorophenyl)-6H-1,3,4-thiadiazine, hydrobromide

The compound 18 was prepared by heating of 1.2 g (0.005 mole) of α-bromo-2-chloroacetophenone with 0.8 g (0.005 mole) of morpholide of thiocarbazinic acid in 30 ml of absolute ethanol for 20 minutes. The mixture was cooled with ice to form a yellow precipitate which was filtered off, recrystallized from absolute ethanol and dried. Yield 1.4 g (76%). M.p. 204–205° C. $R_f$=0.32 (eluent: butanol-acetic acid-water 4:1:5). Found, %: C 41.6; H 4.1; N 11.3. $C_{13}H_{15}BrClN_3OS$. Calculated, %: C 41.4; H 4.0; N 11.2. $^1$H NMR, DMSO-$d_6$, δ, ppm: 3.85 [8H, m, $(CH_2)_2$, morpholino]; 4.25 (2H, s, $SCH_2$); 7.4–7.9 (4H, m, $C_6H_4$).

EXPERIMENTAL BIOLOGICAL PART

The hypometabolic activity of the compounds utilised herein was demonstrated as follows. In all cases tests were carried out on mice of the BALB line of 3–4 month age. Non-toxic doses of compounds under test varying from 60 to 400 mg/kg were used in all experiments. In the case of water-soluble compounds, aqueous solutions of the test compounds were injected intraperitoneally (i.p.), while water-insoluble compounds were introduced orally (p.o.).

In order to demonstrate the effect of the compounds herein on body temperature and oxygen consumption, in-vivo experiments were run using 5–6 mice per dosage.

Rectal temperature changes (absolute magnitues in ° C.) were measured using a medicinal electrothermometer TREM-1 (Table 1). The rate of oxygen consumption was monitored by measuring concentration of oxygen in a closed testing unit with optic-acoustic gas analyser MN 5130. The data on oxygen consumption are given in percents relative to the starting content of oxygen taken as 100%. (Table 2).

When used in non-toxic doses all compounds were found to decrease rectal temperature in the range from 3 to 15° C., depending on the structure, dosage and method of introduction. It has been established that some of the tested compounds show sharp drop in body temperature (7–8 ° C. per 30 minutes) while others demonstrate only moderate effect (7–10° C. per 3 hours) as illustrated in Table 1.

Compound 1 was dissolved in water (30 mg/ml) and injected into mice intraperitoneally in doses varying from 10 up to 365 mg/kg (¹⁄₁₆ $LD_{16}$–$LD_{50}$).

Rectal temperature of mice was followed in dynamics after 5, 15, 30, 60, 120, 180, 240, 300, and 360 minutes (Table 3). The maximum change was observed with doses of 140 and 190 mg/kg, equal calculated and experimental values of ½ $LD_{16}$, respectively, The maximum drop of body temperature (7–8° C.) at 140 mg/kg dosage was observed after 40–60 minutes. The same decrease in temperature at 190 mg/kg dosage was reached after 15 minutes; in 1.5 hours it reached 22–25° C. and maintained this level over the next 5 hours, that is 13–17° C. below the initial value. After one day, body temperature was restored to the value of 94–96% of initial.

The behaviour of mice to injection of compound 1 at 140 mg/kg dosage is as follows:

5 minutes—decrease in motor activity, suppression of breathing; 15–180 minutes—akinesia, mio-relaxation, lack of reflexes; 180–360 minutes—restoration of motor activity. Importantly, the reduction in body temperature at non-toxic dose levels was not accompanied by tremor or convulsions.

The effect of Compound 1 on oxygen consumption is tabulated in Table 3.

TABLE 1

Effects of 1,3,4-thiadiazines on body temperature in experiments on mice

| Compound | Dose, mg/kg (mM/kg) | Administration | Time of measurements in minutes | | | |
|---|---|---|---|---|---|---|
| | | | 0 | 30 | 60 | 90 |
| 1 | 190.0 (0.56) | i.p. | 39.2 | 26.9 | 23.5 | 21.4 |
| 2 | 178.0 (0.50) | i.p. | 38.0 | 30.1 | 26.7 | 25.5 |
| 4 | 437.0 (1.00) | p.o. | 38.0 | 35.9 | 33.8 | 33.5 |
| 5 | 190.0 (0.53) | i.p. | 38.0 | 28.0 | 27.1 | — |
| | 328.0 (0.96) | p.o. | 38.0 | 27.5 | 26.0 | 24.0 |
| 6 | 160.0 (0.43) | i.p. | 37.9 | 30.6 | 26.9 | 26.3 |
| | 407.0 (1.0) | p.o. | 37.7 | 34.0 | 33.4 | 32.6 |

TABLE 1-continued

Effects of 1,3,4-thiadiazines on body temperature in experiments on mice

| Compound | Dose, mg/kg (mM/kg) | Administration | Time of measurements in minutes | | | |
|---|---|---|---|---|---|---|
| | | | 120 | 180 | 240 | 300 |
| 1 | 190.0 (0.56) | i.p. | 23.0 | 20.9 | 21.1 | 20.2 |
| 2 | 178.0 (0.50) | i.p. | 26.9 | 31.0 | 35.4 | 35.4 |
| 4 | 437.0 (1.00) | p.o. | 32.9 | 33.1 | 32.8 | — |
| 5 | 190.0 (0.53) | i.p. | 25.0 | 23.3 | 23.6 | — |
| | 328.0 (0.96) | p.o. | 24.0 | — | — | — |
| 6 | 160.0 (0.43) | i.p. | 25.8 | 27.4 | 28.9 | 30.9 |
| 7 | 407.0 (1.0) | p.o. | 33.5 | 32.3 | 30.6 | 30.6 |
| 8 | 435.0 (1.0) | p.o. | 33.4 | 33.5 | 32.3 | 33.9 |
| 8 | 435.0 (1.0) | p.o. | 38.1 | 35.2 | 35.0 | — |

TABLE 2

Effects of Compound 1 on body temperature (T) and consumption of oxygen ($O_2$) in experiments on mice

| Compound | Dose (1/2 $LD_{16}$) mg/kg (mM/kg) | Index | Time of measurements in minutes | | | | |
|---|---|---|---|---|---|---|---|
| | | | 0 | 5 | 15 | 30 | 60 |
| 1 | 190 (0.56) | T | 39.2 ± 0.1 | 34.9 ± 0.0 | 30.8 ± 0.2 | 26.9 ± 0.4 | 23.5 ± 0.2 |
| | | $O_2$ | 100 | 43 | 71.7 | 49.2 | 29.5 |

| Compound | Dose (1/2 $LD_{16}$) mg/kg (mM/kg) | Index | Time of measurements in minutes | | | | |
|---|---|---|---|---|---|---|---|
| | | | 90 | 120 | 180 | 240 | 300 |
| 1 | 190 (0.56) | T | 21.4 ± 0.2 | 23.0 ± 0.8 | 20.9 ± 0.1 | 21.1 ± 0.1 | 20.2 ± 0.0 |
| | | 100 | 47.5 | 36.9 | 55.3 | 99.6 | 151.6 |

TABLE 3

Dose effects of Compound 1 on body temperature (T) and consumption of oxygen (O2) experiments on mice

| Dose mg/kg (mM/kg) | Index | Time of measurements in minutes | | | | | |
|---|---|---|---|---|---|---|---|
| | | 0 | 10 | 20 | 30 | 40 | 60 |
| 365.0 (1.06) | T | 39.6 ± 0.1 | 35.4 ± 0.2 | 30.1 ± 0.2 | 27.2 ± 0.2 | 25.5 ± 0.2 | 23.3 ± 0.3 |
| | $O_2$ | 100 ± 4.7 | 15.2 ± 3.1 | 15.8 ± 5.0 | 13.6 ± 3.4 | | 13.3 ± 3.7 |
| 279.0 (0.82) | T | 38.9 ± 0.6 | 35.8 ± 0.1 | 30.2 ± 0.1 | 27.1 ± 0.1 | 24.7 ± 0.2 | 21.0 ± 0.1 |
| | $O_2$ | 100 ± 5.2 | 32.6 ± 2.2 | 26.7 ± 2.2 | 20.7 ± 2.2 | | 9.3 ± 5.1 |
| 190.0 (0.56) | T | 39.2 ± 0.1 | 34.9 ± 0.0 | 30.8 ± 0.2 | 26.9 ± 0.4 | 25.9 ± 0.3 | 23.5 ± 0.2 |
| | $O_2$ | 100 ± 27.8 | 26.3 ± 9.8 | 71.7 ± 4.1 | 49.2 ± 8.2 | | 29.5 ± 15.0 |
| 140.0 (0.41) | T | 37.9 ± 0.1 | 34.5 ± 0.2 | 32.6 ± 0.4 | 30.8 ± 0.2 | 30.2 ± 0.1 | 30.0 ± 0.1 |
| | $O_2$ | 100 ± 21.7 | 26.3 ± 6.8 | 46.8 ± 4.7 | 32.2 ± 8.7 | | 49.3 ± 9.8 |
| 70.0 (0.20) | T | 37.5 ± 0.2 | 36.2 ± 0.3 | 35.4 ± 0.5 | 34.5 ± 0.4 | 35.0 ± 0.9 | 35.6 ± 0.6 |
| | $O_2$ | | | | | | |
| 35.0 (0.1) | T | 37.7 ± 0.2 | 37.2 ± 0.2 | 36.6 ± 0.4 | 35.9 ± 0.1 | 36.6 ± 0.1 | 37.0 ± 0.3 |
| | $O_2$ | 100 ± 7.4 | 86.3 ± 13.1 | 73.6 ± 2.6 | 68.4 ± 8.0 | | 70.4 ± 7.1 |
| 10.0 (0.05) | T | 37.5 ± 0.2 | 37.8 ± 0.1 | 37.4 ± 0.2 | 37.3 ± 0.1 | 37.5 ± 0.1 | 37.5 ± 0.1 |
| | $O_2$ | 100 ± 6.9 | 94.0 ± 5.5 | 87.3 ± 9.9 | 78.2 ± 4.6 | | 83.3 ± 18.1 |

| Dose mg/kg (mM/kg) | Index | Time of measurements in minutes | | | | | |
|---|---|---|---|---|---|---|---|
| | | 90 | 120 | 180 | 210 | 240 | 270 |
| 365.0 (1.06) | T | 21.5 ± 0.2 | 20.9 ± 0.2 | 21.4 ± 0.1 | 21.2 ± 0.0 | 21.1 ± 0.0 | 21.4 ± 0.7 |
| | $O_2$ | 13.1 ± 2.0 | 17.0 ± 3.4 | 11.2 ± 3.4 | | 8.2 ± 2.0 | |
| 279.0 (0.82) | T | 20.0 ± 0.1 | 21.0 ± 0.3 | 21.2 ± 0.2 | 21.2 ± 0.1 | 20.8 ± 0.1 | 21.5 ± 0.1 |
| | $O_2$ | 10.9 ± 5.5 | 9.3 ± 5.9 | 9.3 ± 4.0 | | 13.0 ± 8.7 | |

TABLE 3-continued

Dose effects of Compound 1 on body temperature (T) and consumption of oxygen (O2) experiments on mice

| 190.0 (0.56) | T | 21.4 ± 0.2 | 23.0 ± 0.8 | 20.9 ± 0.1 | 21.4 ± 0.1 | 21.1 ± 0.1 | 20.8 ± 0.3 |
|---|---|---|---|---|---|---|---|
| | O$_2$ | 47.5 ± 6.8 | 36.9 ± 22.8 | 55.3 ± 9.1 | | 99.6 ± 11.2 | |
| 140.0 (0.41) | T | 31.5 ± 0.9 | 33.6 ± 0.7 | 35.2 ± 0.5 | 36.1 ± 0.4 | 36.5 ± 0.2 | 36.6 ± 0.2 |
| | O$_2$ | 43.6 ± 18.6 | 49.3 ± 15.4 | 78.9 ± 10.6 | | 88.8 ± 9.8 | |
| 70.0 (0.20) | T | 36.1 ± 0.2 | 37.0 ± 0.2 | 36.7 ± 0.6 | 36.9 ± 0.2 | 37.0 ± 0.1 | 36.6 ± 0.2 |
| 35.0 (0.1) | T | 37.3 ± 0.1 | 37.1 ± 0.3 | 36.9 ± 0.2 | 36.6 ± 0.1 | 36.9 ± 0.4 | 36.8 ± 0.1 |
| | O$_2$ | 72.1 ± 10.4 | 68.4 ± 11.2 | 78.4 ± 9.3 | | 97.4 ± 5.6 | |
| 10.0 (0.05) | T | 37.4 ± 0.2 | 36.9 ± 0.1 | 36.9 ± 0.2 | 36.4 ± 0.2 | 36.7 ± 0.2 | 36.7 ± 0.2 |
| | O$_2$ | 75.9 ± 19.3 | 95.6 ± 10.8 | 80.6 ± 9.9 | | 92.6 ± 3.9 | |

| Dose mg/kg (mM/kg) | Index | Time of measurements in minutes | | | | | |
|---|---|---|---|---|---|---|---|
| | | 300 | 330 | 390 | 1140 | 1620 | 1980 |
| 36.5 (1.06) | T | 22.1 ± 0.0 | 21.5 ± 0.1 | 20.0 ± 0.2 | 20.8 ± 0.3 | 21.6 ± 0.1 | 22.1 ± 0.2 |
| | O$_2$ | 18.4 ± 2.0 | | | | | |
| 279.0 (0.82) | T | 21.3 ± 0.3 | 22.5 ± 0.3 | 19.4 ± 0.3 | 20.8 ± 0.4 | 22.6 ± 0.9 | 21.2 ± 0.3 |
| | O$_2$ | 10.9 ± 1.0 | | | | | |
| 190.0 (0.56) | T | 20.2 ± 0.2 | 19.8 ± 0.2 | 19.8 ± 0.2 | 36.9 ± 0.3 | 37.9 ± 0.4 | 36.9 ± 0.3 |
| | O$_2$ | 151.6 ± 20.7 | | | | | |
| 140.0 (0.41) | T | 36.9 ± 0.1 | 37.6 ± 0.2 | 37.2 ± 0.2 | | | |
| | O$_2$ | 105.3 ± 20.5 | | | | | |
| 70.0 (0.20) | T | 37.0 ± 0.1 | 37.2 ± 0.1 | 37.1 ± 0.1 | | | |
| | O$_2$ | | | | | | |
| 35.0 (0.1) | T | 36.9 ± 0.1 | 37.2 ± 0.2 | 37.1 ± 0.1 | | | |
| | O$_2$ | 85.1 ± 3.8 | | | | | |
| 10.0 (0.05) | T | 36.9 ± 0.1 | 36.8 ± 0.2 | 36.7 ± 0.2 | | | |
| | O$_2$ | 109.7 ± 8.8 | | | | | |

What is claimed is:

1. A method for retarding metabolism in a patient so as to reduce the body temperature, oxygen intake or both of the patient, said method comprising administering to the patient an amount effective for said regulation of a 6H-1,3,4-thiadiazin-2-amine of the following formula:

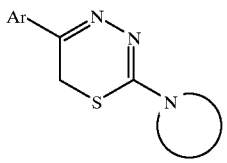

wherein Ar is phenyl optionally substituted with one or more chloro, bromo atoms, $C_1$–$C_4$ alkoxy or $C_1$–$C_4$ alkyl groups; and

represents a morpholino, thiomorpholino, piperidino, pyrrolidino, or hexamethyenimino moiety, or a pharmaceutically acceptable salt thereof.

2. A method as claimed in claim 1 wherein the 6H-1,3,4-thiadiazin-2-amine is selected from the consisting of group:
2-morpholino-5-(4-chlorophenyl)-6H-1,3,4-thiadiazine,
2-morpholino-5-(3-bromophenyl)-6H-1,3,4-thiadiazine;
2-thiomorpholino-5-phenyl-6H-1,3,4-thiadiazine;
2-thiomorpholino-5-(4-ethoxyphenyl)-6H-1,3,4-thiadiazine;
2-thiomorpholino-5-(3-bromophenyl)-6H-1,3,4-thiadiazine;
2-thiomorpholino-5-(4-methoxypenyl)-6H-1,3,4-thiadiazine;
2-thiomorpholino-5-(2-chlorophenyl)-6H-1,3,4-thiadiazine;
2-thiomorpholino-5-(4-chlorophenyl)-6H-1,3,4-thiadiazine;
2-hexamethylenimino-5-phenyl-6H-1,3,4-thiadiazine;
2-piperidono-5-phenyl-6H-1,3,4-thiadiazine;
2-pyrrolidino-5-phenyl-6H-1,3,4-thiadiazine;
2-hexamethylenimino-5-(4-bromophenyl)-6H-1,3,4-thiadiazine;
2-hexamethylenimino-5-(4-chlorophenyl)-6H-1,3,4-thiadiazine;
2-morpholino-5-(2-chlorophenyl)-6H-1,3,4-thiadiazine; and pharmaceutically acceptable salts thereof.

3. A method as claimed in claim 1, wherein the 6H-1,3,4-thiadiazin-2-amine is administered to the patient in an amount effective to reduce the body temperature of the patient.

4. A method as claimed in claim 1, wherein the 6H-1,3,4-thiadiazine-2-amine is administered to the patient in an amount effective to reduce the oxygen consumption of the patient.

* * * * *